US007662294B1

(12) United States Patent
Cox, Jr.

(10) Patent No.: US 7,662,294 B1
(45) Date of Patent: Feb. 16, 2010

(54) METHOD FOR REDUCING ORGANIC CONTAMINATION

(76) Inventor: Henry Wilmore Cox, Jr., 1103 Kam Dr., Blacksburg, VA (US) 24060

( * ) Notice: Subject to any disclaimer, the term of this patent is extended or adjusted under 35 U.S.C. 154(b) by 416 days.

(21) Appl. No.: 11/047,879

(22) Filed: Feb. 1, 2005

Related U.S. Application Data

(60) Provisional application No. 60/558,936, filed on Apr. 2, 2004, provisional application No. 60/541,378, filed on Feb. 2, 2004.

(51) Int. Cl.
*C02F 1/72* (2006.01)
*C02F 1/76* (2006.01)
*A62D 3/33* (2007.01)
*A62D 3/38* (2007.01)

(52) U.S. Cl. .................. 210/759; 210/753; 210/764; 210/909; 588/315; 588/320; 588/405

(58) Field of Classification Search ............... 210/758, 210/753, 759, 760, 764, 909; 134/22.1, 22.11, 134/22.14, 22.19, 42; 405/128.5; 588/315, 588/320, 405
See application file for complete search history.

(56) References Cited

U.S. PATENT DOCUMENTS

| | | | |
|---|---|---|---|
| 3,966,600 A | | 6/1976 | Crowley et al. |
| 4,167,405 A | * | 9/1979 | Mues et al. .................... 71/27 |
| 4,363,215 A | | 12/1982 | Sharp |
| 4,686,067 A | * | 8/1987 | Veysset et al. ............... 376/310 |
| 4,729,855 A | * | 3/1988 | Murray et al. ................. 134/2 |
| 4,960,576 A | | 10/1990 | Bedell |
| 5,019,131 A | | 5/1991 | Nitsch |
| 5,232,484 A | | 8/1993 | Pignatello |
| 5,286,141 A | | 2/1994 | Vigneri |
| 5,368,830 A | | 11/1994 | Alfano et al. |
| 5,476,992 A | * | 12/1995 | Ho et al. ..................... 588/302 |
| 5,520,483 A | | 5/1996 | Vigneri |
| 5,741,427 A | | 4/1998 | Watts |
| 5,849,950 A | | 12/1998 | Greindl |
| 5,850,086 A | | 12/1998 | Que |
| 5,929,012 A | | 7/1999 | Del Duca |
| 6,063,346 A | | 5/2000 | Luna |
| 6,100,297 A | | 8/2000 | Weglicki |
| 6,160,194 A | | 12/2000 | Pignatello |
| 6,254,312 B1 | | 7/2001 | Chowdhury et al. |
| 6,271,191 B1 | * | 8/2001 | Kerobo et al. ............... 510/475 |
| 6,319,328 B1 | | 11/2001 | Greenberg |
| 6,960,330 B1 | * | 11/2005 | Cox, Jr. ...................... 423/226 |

OTHER PUBLICATIONS

Greenberg, "In-Situ Fenton-Like Oxidation of Volatile Organics: Laboratory, Piolot, and Full-Scale Demonstrations", Jan. 1, 1998. pp. 29-42. Remediation. John Wiley & Sons. Inc.

Interstate Technology and Regulatory Work Group in Situ Chemical Oxidation Work Team. "Technical and Regulatory Guidance for in Situ Chemical Oxidation of Contaminated Soil and Groundwater". Jun. 1, 2001.
Johnson, "Round Up the Usual Suspects". Jan. 22, 1996. Forbes Science and Technology,.
Leung, "Degradation of Perchloroethylene by Fenton's Reagent: Speciation and Pathway". Jul. 1, 1992. pp. 377-381. Journal of Environmental Quality. vol. 21.
Masten, "Ozonation of VOC's in the Presence of Humic Acid and Soils", Jan. 1, 1991. pp. 287-312. NSI Technology Services Corp..
"BOD and COD Reduction Using Hydrogen Peroxide", Feb. 10, 2002, US Peroxide of Laguna Niguel, CA. www.h2o2.com/applications/ industrialwastewater/bodcod.html.
"Chlorinated Solvents Treatment", Feb. 10, 2002. Hydroxyl Systems of Sidney, British Columbia, Canada, www.hydroxyl.com/ind_06.html.
"Fenton's Reagent - Iron-Catalyzed Hydrogen Peroxide", Feb. 10, 2002, US Peroxide, Laguna Niguel, CA. www.h2o2.com/applications/industrialwastewater/ fentonsreagent.html.
"Ground Water Treatment Hydrogen Sulfide Removal", Feb. 10, 2002. US Peroxide of Laguna Niguel, CA, www.h2o2.com/applications/municipaldrinkingwater/h2sremoval.html.
"Groundwater Treatment", Feb. 10, 2002, Hydroxyl Systems of Sidney, British Columbia, Canada, www.hydroxyl.comiind_04.html.
"Inorganic Pollutant Arsenic Removal". Feb. 10, 2002. US Peroxide of Laguna Niguel, CA, www.h2o2.com/applications/industrialwastewater/arsenic.html.
"Inorganic Pollutant Dechlorination with Hydrogen Peroxide". Feb. 10, 2002, US Peroxide of Laguna Niguel. CA. www.h2o2.com/applications/industrialwastewater/dechlorination.html.
"Inorganic Pollutant Nitrogen Oxides (nox) Abatement with Hydrogen Peroxide", Feb. 10, 2002, US Peroxide of Laguna Niguel, CA, www.h2o2.com/applications/industrialwastewater/nox.html.
"Inorganic Pollutant Sulfide Oxidation Using Hydrogen Peroxide". Feb. 10, 2002. US Peroxide of Laguna Niguel, CA, www.h2o2.com/applications/industrialwastewater/sulfideoxidation.html.
"Introduction to Hydrogen Peroxide". Feb. 10, 2002, US Peroxide of Laguna Niguel, CA, www.h202./intro/overview.html.
"Landfill Leachate Treatment Systems". Feb. 10, 2002. Hydroxyl Systems of Sidney. British Columbia. Canada, www.hydroxyl.com/ind07.html.
"Organic Pollutant Formaldehyde Oxidation", Feb. 10, 2002. US Peroxide of Laguna Niguel, CA, www.h2o2.com/applications/industrialwastewater/hcho.html.
"Photographic Waste Treatment with Hydrogen Peroxide". Feb. 10, 2002. US Peroxide of Laguna Niguel, CA, www.h2o2.com/applications/industrialwastewater/photowaste.html.

(Continued)

*Primary Examiner*—Lorna M. Douyon
(74) *Attorney, Agent, or Firm*—Michael Haynes PLC; Michael N. Haynes (57) ABSTRACT

Certain exemplary embodiments provide methods for reducing a concentration of a contaminant associated with a medium, which can be any substance or material, such as soil, water, air, and/or fluid. In one exemplary method, the medium is treated with a ferric chelate and an oxidizing agent in amounts effective to oxidize at least a portion of the contaminant.

21 Claims, 2 Drawing Sheets

OTHER PUBLICATIONS

"Soil Treatment - In situ chemical oxidation of contaminated soils (using hydrogen peroxide)". Feb. 10, 2002, US Peroxide of Laguna Niguel, CA, www.h2o2.com/applications/hazardouswaste/soil.html.

"Surface Water Treatment Residual Ozone Destruction". Feb. 10, 2002. US Peroxide of Laguna Niguel, CA, www.h2o2.com/applications/municipaldrinkingwater/ozonedesta-uction.html.

Pardieck. "Hydrogen Peroxide Use to Increase Oxidant Capacity for in Situ Bioremediation of Contaminated Soils and Aquifers: A Review", Jan. 1, 1992, pp. 221-242, Journal of Contaminant Hydrology, No. 9. Elsevier Science Publishers, B.V., Amsterdam.

Pignatello, "Ferric Complexes as Catalysts for "Fenton" Degradation of 2,4-D and Metolachlor in Soil". Mar. 1, 1994, pp. 365-370. Journal of Environmental Quality, vol. 23. No. 2.

Sun, "Chemical Treatment of Pesticide Wastes. Evaluation of Fe(III) Chelates for Catalytic Hydrogen Peroxide Oxidation of 2,4-D at Circumneutral pH", Feb. 1, 1992, pp. 322- 327, Journal of Agricultural and Food Chemistry, vol. 40, American Chemical Society.

Teel, "Comparison of Mineral and Soluble Iron Fenton's Catalysts for the Treatment of Trichloroethylene", Jan. 1, 2001, pp. 977-984, Water Research, vol. 35, No. 4 by Elsevier Science Ltd. Great Britain.

Tyre. "Waste Management", Oct. 1, 1991, pp. 832-838, Journal of Environmental Quality, vol. 20.

U.S. Environmental Protection Agency, "Field Applications of In Situ Remediation Technologies: Chemical Oxidation", Sep. 1, 1998, Washington, D.C.

Watts, "Hazardous Wastes Assessment, Management, and Minimization", Jun. 1, 1994, pp. 435-440, Water Environment Research, vol. 66, No. 4.

Watts, "Use of Iron Minerals in Optimizing the Peroxide Treatment of Contaminated Soils", Nov. 1, 1993, pp. 839-844, Water Environment Research, vol. 65, No. 7.

Fischer, "Utilization of Biomass Residues for the Remediation of Metal-Polluted Soils", Jun. 4, 1998, pp. 2154-2160, Environmental Science and Technology, vol. 32, No. 14.

Guilbault, "The Application of Modified Nernstian Equations to the Electrochemical Determination of Enzyme Kinetics", Sep. 1, 1963, pp. 1747-1749, Journal of Physical Chemistry, vol. 67, No. 9.

Gustafson, "Hydrolytic Tendencies of Ferric Chelates", Mar. 1, 1963, Journal of Physical Chemistry, vol. 67, pp. 576-582.

Huang, "Synergistic Catalysis of Dimetilan Hydrolysis by Metal Ions and Organic Ligands", Aug. 25, 2000, pp. 4117-4122, American Chemical Society, Environmental Science & Technology, vol. 34, No. 19.

Iupac, "Mini Database of Selected Stability Constants, Academic Software", Software downloaded from: http://www.acadsoft.co.uk; screenshot printed Jul. 10, 2008.

Jungbunzlauer, "Sodium Gluconate", accessed Jul. 1, 2008: http://www.jungbunzlauer.com/products-applications/products/gluconates/sodiumgluconate/general-information.html.

Korendovych, "Dioxygen Activation at Non-Heme Iron: Insights from Rapid Kinetic Studies", May 24, 2007, pp. 510-521, American Chemical Society, Accounts of Chemical Research, vol. 40, No. 7.

Leising, "Alkane Functionalization by Non-Porphyrin Iron Complexes: Mechanistic Insights", Jan. 1, 1990, pp. 2553-2555, American Chemical Society, Inorganic Chemistry, vol. 29, No. 14.

Lin, "Antioxidative Ability of Lactic Acid Bacteria ", Mar. 23, 1999, pp. 1460-1466, American Chemical Society, Journal of Agriculture and Food Chemistry, vol. 47, No. 4.

Motekaitis, "Complexes of Aluminum (III) with Hydroxy Carboxylic Acids", Jan. 1, 1984, pp. 18-23, American Chemical Society, Inorganic Chemistry vol. 23, No. 1.

Murthi, "Mg-Gluconate provides superior protection against postischemic dysfunction and oxidative injury compared to Mg-sulfate Abstract ", Mar. 1, 2003, pp. 141-148, Molecular and Cellular Biochemistry, vol. 245, Nos. 1-2.

National Institute of Standards and Technology, "Nist Database 46: Critically Selected Stability Constants ", Jun. 1, 2002, downloaded as a program from their website at [http://www.nist.gov/srd/nist46.htm].

NIST PUBCHEM, "Ferric Gluconate" NIST PubChem (Public Chemical) database, accessed Jul. 1, 2008 from http://pubchem.ncbi.nlm.nih.gov/summary/summary.cgi?sid=7849072&loc=ec_rcs.

OECD SIDS, "United Nations Environment Programme Chemicals Branch: Screening Information Datasets for High Volume Chemicals, Gluconates—Gluconic Acid and Its Derivatives", Jan. 25, 2006, 231 pages.

Pecsok, "The Gluconate Complexes II - The Ferric-Gluconate System", Mar. 20, 1955, pp. 1489-1494, Journal of the American Chemical Society, vol. 77.

Proskouriakoff, "An Iron Compound of Gluconic Acid", Apr. 1, 1934, pp. 996-997, Journal of the American Chemical Society, vol. 56, No. 4.

Que, "A Highly Reactive Functional Model for the Catechol Dioxygenases. Structure and Properties of [Fe( TPA)DBC]BPh4", Jan. 1, 1991, pp. 9200-9204, Journal of the American Chemical Society, 1991, vol. 113, No. 24.

Richert, "Ligand-Centered Oxidation of Manganese (II) Complexes", Jan. 1, 1998, pp. 1814-1818, Inorganic Chemistry, 1998, vol. 27, No. 10.

Rodriguez, "A New Tripodal Tetradentate Ligand and Its Iron (III) Complex, as a Model for Mononuclear Non-Heme Iron Active sites. Reactivity Studies toward Dioxygen and Superoxide", Jan. 1, 1996, pp. 7804-7810, American Chemical Society, Inorganic Chemistry, 1996, vol. 35, No. 26.

Sawyer, "Metal Gluconate Complexes", Apr. 3, 1964, pp. 633-643, Chemical Revues, vol. 64, No. 6.

Strlic, "Anti- and Prooxidative Properties of Gallic Acid in Fenton-Type Systems", Sep.27, 2002, pp. 6313-6317, Journal of Agricultural and Food Chemistry, vol. 50.

Tajmir-Riahi , "Carbohydrate metal ion complexes. Interaction of D-glucono-1,5- lacctone with Zn(II), Cd(II) and Hg(II) ions in the solid and aqueous solution, studied by 13C-NMR, FT-IR spectroscopy and X-ray powder diffraction measurements", Jan. 1, 1989, pp. 651-654, Canadian Journal of Chemistry, vol. 67.

Westall, "Models for Association of Metal Ions with Heterogeneous Environmental Sorbents. 1 .Complexation of Co(II) by Leonardite Humic Acid as a Function of pH and NaC 104 Concentration", Jan. 1, 1995, pp. 951-959, Environmental Science & Technology, vol. 29, No. 4.

Xu, "Mechanisms of wood degradation by brown-rot fungi: chelator-mediated cellulose degradation and binding of iron by cellulose", Jan. 1, 2001, pp. 43-57, Journal of Biotechnology, 2001, vol. 87.

Martell, "Hydrolytic Tendencies of Ferric Chelates", Mar. 1, 1963, pp. 576-582, Journal of Physical Chemistry, vol. 67.

Nih, "Nitrilotriactetic Acid", 2 pages, initially downloaded on Dec. 16, 2008 from: http://ntp.niehs.nih.govintp/roc/eleventh/profiles/s119nitr.pdf.

Nih PubChem, "Ferric NTA", 3 pages, accessed Dec. 21, 2008 at: http://pubchem.ncbi.nlm.nih.gov.

Sawyer, "Ligand-Centered Oxidation of Manganese(II) Complexes", May 1, 1998, pp. 1814-1818, Inorganic Chemistry, vol. 27.

* cited by examiner

METHOD FOR REDUCING ORGANIC CONTAMINATION

CROSS REFERENCE TO RELATED APPLICATIONS

This application claims priority to, and incorporates by reference in its entirety, the following pending provisional U.S. patent applications:
Ser. No. 60/541,378, filed 2 Feb. 2004; and
Ser. No. 60/558,936, filed 2 Apr. 2004.

BRIEF DESCRIPTION OF THE DRAWINGS

Certain exemplary embodiments will be more readily understood through the following detailed description, with reference to the accompanying drawings, in which.

DETAILED DESCRIPTION

Certain exemplary embodiments provide compositions, methods, and/or systems, some of which can be useful for remediating contamination. Certain exemplary embodiments can be useful for reducing a concentration of a contaminant associated with a medium by treating the medium with ferric gluconate (Fe-GLC) and an oxidizing agent in amounts effective to oxidize at least a portion of the contaminant.

It is not currently known with certainty exactly how certain embodiments cause the reduction in concentration of the contaminant, and particularly, the precise reaction mechanism is currently unproven. Nevertheless, several potential theories to describe the mechanism of the reaction are recognized.

According to certain theories, hydroxyl radicals, free radicals, or both react with and degrade at least the target contaminant. As a foundation for these theories, it is recognized that numerous contaminated media, including soil and water, can be treated by the application of oxidants. The following table lists several oxidants and their oxidation potential:

TABLE 1

Oxidation Potential of Various Oxidants

| Oxidant | Oxidation Potential, V |
|---|---|
| Fluorine | 3.0 |
| Hydroxyl radical | 2.8 |
| Ozone | 2.1 |
| Hydrogen peroxide | 1.8 |
| Potassium permanganate | 1.7 |
| Chlorine dioxide | 1.5 |
| Chlorine | 1.4 |

As shown in preceding table, hydrogen peroxide is a relatively powerful oxidant. Also shown in the preceding table is the much more powerful hydroxyl radical, a type of free radical, which is second in the list only to fluorine in its oxidation potential. During certain oxidation processes, such as those involving hydroxyl and/or other free radicals, organic contaminants can be completely, or nearly completely mineralized to carbon dioxide, oxygen, water, and a small amount of mineral acids or salts.

For example, hydroxyl radicals can destroy phenols, MtBE, BTEX (benzene-toluene-ethylbenzene-xylenes), pesticides, solvents, plasticizers, chelants, chloroethenes, petroleum hydrocarbons, BOD and COD (biological oxygen demand/chemical oxygen demand) contributing compounds, and virtually any other organic requiring treatment. Moreover, hydroxyl radicals can atmospherically degrade polyfunctional oxygenated compounds, such as diethers and hydroxyethers, as well as aliphatic alcohols, ethers, carbonyls, ketones, and alkanes. Further, hydroxyl radicals can disinfect process waters and biological effluents, and can decompose amino acids.

Also, hydroxyl radicals can treat water containing chemical warfare agents (e.g., Sarin, Tabun, VX, GF, GX, Cyanide, Soman, mustard gas, etc.); pathogens & biological warfare agents (e.g., bacteria, viruses, anthrax, cryptosporidium, etc.); soil and water contaminants (e.g., MtBE, EtBE, BTEX, chlorinated solvents, DCA, TCA, haloalkanes, methylene chloride, NDMA, carbon tetrachloride, haloalkenes, vinyl chloride, DCE, TCE, PCE, chloroform, acetones, ketones, cyanides, acrylonitriles, phenols, formaldehyde, alcohols, glycol ethers, etc.); ordnance, propellants, and energetic compounds (e.g., TNT, RDX, NDMA, etc.); pharmaceutical residuals (e.g., endocrine disruptors, estrogen, antibiotics, etc.); and/or pesticides (e.g., Dieldrin, Atrazine, IPC, 2,4-D, DDT, etc.), etc.

Hydroxyl radicals can be generated during processes involving the catalyzed activation of hydrogen peroxide using such metals as iron, copper, manganese, and/or other transition metal compounds. One group of such processes is Fenton-type chemical reaction systems, which employ ferrous salts and hydrogen peroxide in acidified (pH ~2 to 3) soil or water suspensions.

In the classic Fenton reaction (Equation 1, below), ferrous ion rapidly reduces hydrogen peroxide to primarily hydroxyl radicals, which can react with and degrade a target contaminant. The reaction involves hydrogen peroxide and a ferrous iron catalyst. The peroxide is broken down into a hydroxide ion and a hydroxyl free radical. The hydroxyl free radical is the primary oxidizing species and can be used to oxidize and break apart organic molecules.

$$H_2O_2 + Fe^{2+} \rightarrow Fe^{3+} + HO^- + HO^* \qquad \text{(Equation 1)}$$

In the classic Fenton reaction, ferrous ion is required in stoichiometric amounts. Peroxide demand, and therefore, ferrous ion demand can be high in certain media, such as soil for example, due to competitive oxidation of soil organic matter and soil-catalyzed decomposition. Ferrous ion also can be oxidized by the hydroxyl radicals, and therefore can compete with the target compounds unless its concentration is kept low by gradual addition in dilute form.

Ferric ion can also produce hydroxyl radicals from peroxide, albeit at a slower rate than ferrous ion. The use of ferric ion, however, typically requires acidic conditions to keep the iron soluble; the reaction has an optimum pH of about 3. In certain media, such as soil for example, acidification to an optimum pH of 3 can be challenging because soil can have a high buffering capacity. Moreover, because acidification itself can be viewed in at least some circumstances as a polluting practice, in some cases the soil must be excavated for treatment and neutralized before replacement. Similar concerns can exist for processes causing the acidification of contaminated water, air, vapors, and/or surfaces.

As used herein, the term "ferric chelate" means any one of a number of organic and inorganic polydentate ligands complexed with ferric ion, Fe(III). An "active" ferric chelate is one that exhibits activity toward oxidation of the contaminant to be degraded, i.e., is capable of generating free radicals or other reactive oxidants from reacting with an oxidizing agent, such as a peroxide or a persulfate. An "oxidizing agent" is a substance that, when reacted with an active ferric chelate, results in the creation of reactive oxidants, such as free radicals.

Certain exemplary embodiments are based, at least in part, on the surprising discovery that a particular novel active ferric chelate, Fe-GLC, and selected oxidizing agents unpredictably demonstrate significant activity at oxidizing contaminants associated with a medium above and beyond the activity which would be expected in the presence of the selected oxidizing agent alone.

Thus, certain exemplary embodiments comprise a method for reducing a concentration of a contaminant associated with a medium, comprising treating the medium with Fe-GLC and an oxidizing agent in amounts effective to oxidize at least a portion of the contaminant.

The oxidizing agent can be a peroxide, such as hydrogen peroxide, calcium peroxide, and/or magnesium peroxide, etc.; a persulphate, such as sodium persulphate, potassium persulphate, and/or ammonium persulphate, etc; ozone; a permanganate, such as sodium permanganate, potassium permanganate, etc; chlorine dioxide; a perchlorate, such as ammonium perchlorate, potassium perchlorate, etc.; and/or a halogen, such as chlorine, bromine, iodine, and/or fluorine, etc.

The medium can be any substance or material, such as solids, water, air, and fluid. For example, the medium can be a naturally occurring solid, such as earth, soil, clay, dust, sand, gravel, stone, rock, sediment, and/or activated charcoal. As another example, the medium can be any solid that is considered a waste, such as rubbish, trash, refuse, medical waste, radioactive waste, sweepings, scourings, rubble, debris, detritus, scum, grease, sludge, sewage, jetsam, and/or flotsam, etc.

As a yet another example, the medium can be any liquid, such as water, groundwater, leachate, wastewater, sewer water, blackwater, graywater, bilge water, ballast water, feed water, process water, industrial water, irrigation water, recreational water, pond water, lake water, creek water, river water, rain water, runoff water, pool water, cooling water, non-potable water, potable water, drinking water, semi-pure water, and/or spent ultra-pure water, etc.

As a further example, the medium can be any fluid, such as air, vapor, liquid, exhaust, and/or vent gas, etc. Moreover, the fluid can occupy a space defined at least in part by a structure, such as for example, a tunnel, mine, well, ditch, canyon, cavern, cave, hole, corner, niche, bunker, building, compartment, room, clean room, enclosure, container, tank, pipe, equipment, ship, airplane, vehicle, automobile, and/or train, etc.

Moreover, the medium can be any surface, including a surface of a building, compartment, facility, pavement, floor, flooring material, wall, divider, corner, door, window, shade, ceiling, roof, lid, tent, tarp, casing, envelope, covering, skin, wrapper, sheathing, veneer, surface, substrate, tray, ledge, shelf, container, fixture, appliance, equipment, machine, mechanism, apparatus, device, furniture, furnishing, protective gear, clothing, footwear, safety equipment, military product, military equipment, industrial product, industrial equipment, commercial product, commercial equipment, consumer product, consumer equipment, unfinished product, unfinished equipment, laboratory equipment, laboratory device, laboratory supply, medical equipment, medical device, medical supply, decontamination chamber, vessel, storage tank, pipe, valve, pump, blower, tubing, duct, conveyance system, silo, tanker, well, and/or oil well, etc.

The contaminant can be any contaminating substance that can be oxidized, such as, for example, a chemical compound, chemical mixture, organic compound, inorganic compound, hydrogen sulfide, and/or biological, etc. As a further example, the contaminant can be an organic compound, an organic compound having at least one aromatic functional group, and/or an organic compound having at least one aliphatic functional group, etc.

As yet another example, the contaminant can be gasoline, MtBE, EtBE, BTEX (benzene-toluene-ethylbenzene-xylenes), chlorobenzene, chlorotoluene, dichlorobenzene, dichloroethene, tetrachloroethene, trichloroethene, benzo (a) pyrene, benzo (b) fluoranthene, benzo (k) fluoranthene, chrysene, dibenz (a,h) anthracene, indeno (1,2,3-cd) pyrene, cis-dichloroethene, trans-dichloroethene, hydrazine, and/or diaminotoluene; phenol; chlorinated solvents, DCA, TCA, haloalkanes, methylene chloride, NDMA, carbon tetrachloride, haloalkenes, vinyl chloride, DCE, TCE, PCE, chloroform, acetones, ketones, cyanides, acrylonitriles, phenols, formaldehyde, alcohols, glycol ethers, chlorinated solvents (e.g., polychlorinated biphenyls (PCBs), pentachlorophenol (PCP), etc.), chemical warfare agents (e.g., Sarin, Tabun, VX, GF, GX, Cyanide, Soman, mustard gas, etc.), ordnance, propellants, and energetic compounds (e.g., TNT, RDX, NDMA, etc.), human and/or animal drugs and/or pharmaceuticals (e.g., endocrine disruptors, estrogen, steroids, antibiotics, pain relievers, caffeine, etc.), pesticides (including any compound used to deter and/or destroy pests, including herbicides, fungicides, insecticides, rodenticides, and the like, e.g., Dieldrin, Atrazine, IPC, 2,4-D, DDT, N-N-diethyltoluamide, etc.), plasticizers, chelants, fire retardants (e.g., tri (2-chloroethyl) phosphate), disinfectants (e.g., triclosan), detergent metabolites (e.g., 4-nonylphenol), chloroethenes, petroleum hydrocarbons, BOD and COD (biological oxygen demand/chemical oxygen demand) contributing compounds, polyfunctional oxygenated compounds, such as diethers and hydroxyethers, as well as aliphatic alcohols, ethers, carbonyls, ketones, alkanes, naphthalenes, lubricants, cyanides, complex cyanides, mercaptans, and/or virtually any other organic requiring treatment, etc.

Furthermore, the contaminant can be a biological, such as any lifeform, pest, plant, invertebrate, mollusk, nematode, insect, parasite, mold, fungi, protozoa, amoeba, bacteria, virus, prion, protein, and/or amino acid, etc., including pathogens and biological warfare agents such as for example, smallpox, Ebola, cholera, typhoid, anthrax, plague, and/or cryptosporidium, etc.

Numerous embodiments are possible. The following exemplary embodiments are intended to merely illustrate, and not limit, the breadth and depth of embodiments that can fall within the scope of the appended claims and future claims.

Method 100

Figure 1:
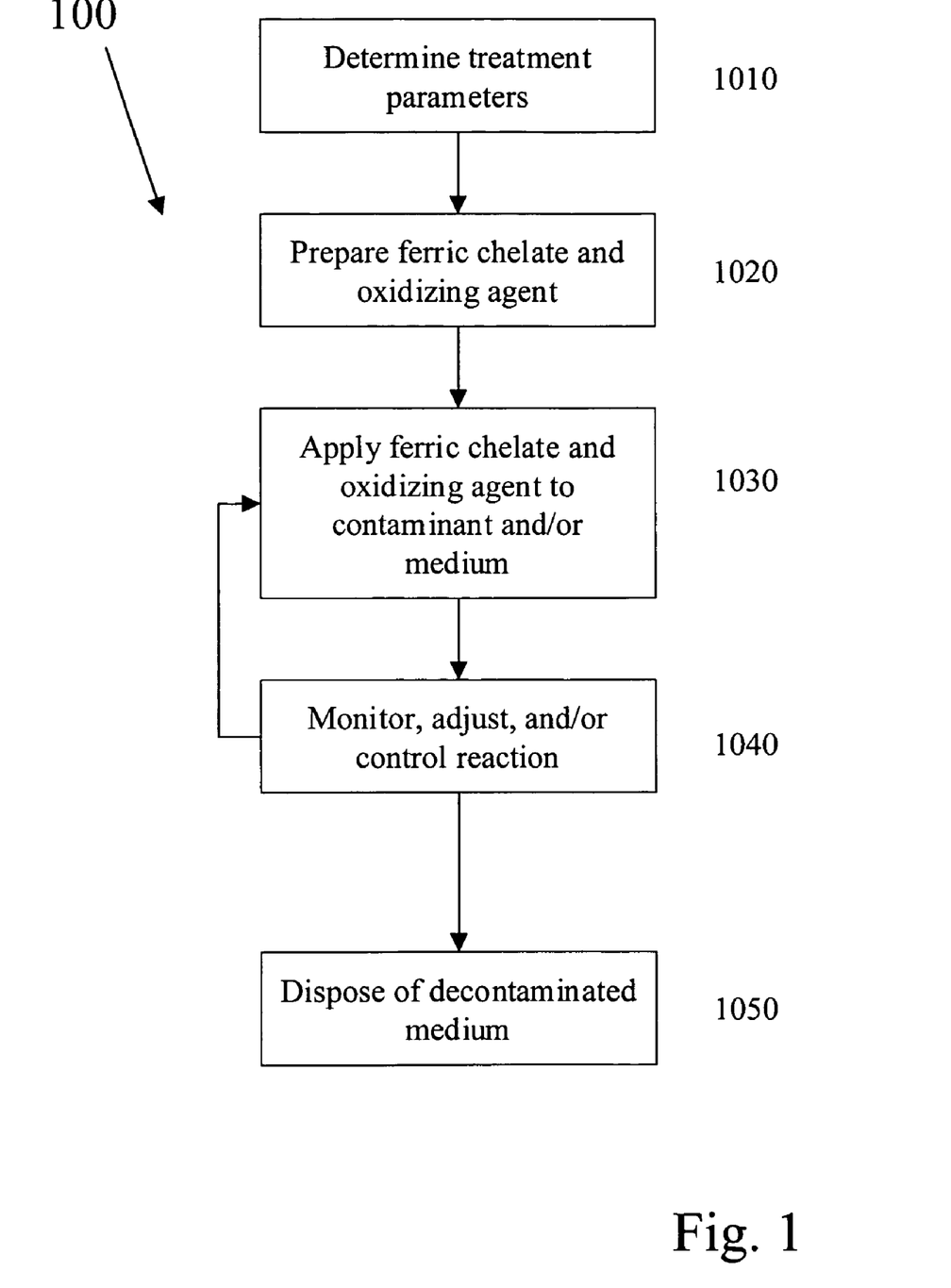
FIG. 1 is a flowchart of an exemplary embodiment of a method 100.

FIG. 1 is a flowchart of an exemplary embodiment of a method 100, which can begin at activity 1010 by determining the treatment parameters. Included in this determination can be activities such as sampling the medium to detect if a contaminant is present, analyzing the sample or the medium to identify the contaminant(s) and/or to determine what concentrations of the contaminant are present, determining an amount of the medium to treat, determining where to treat the medium (e.g., in situ, ex situ, or both), and/or determining one or more operating parameters, e.g., temperatures, pressures, amounts, and/or flowrates, of the medium, the Fe-GLC, and/or the oxidizing agent.

At activity 1020, effective amounts of the Fe-GLC and/or the oxidizing agent can be prepared. One method of preparing Fe-GLC is to directly mix with GLC a source of ferric ion, such as an aqueous solution of a ferric salt, such as ferric perchlorate, ferric nitrate, ferric citrate, ferric malate, ferric lactate, and/or ferric oxalate, etc. Another method is to mix a liquid ferric chloride solution with GLC. Ferric chloride can be purchased as a ~13% ferric solution with a pH of about 1.0 to about 1.5 from Univar, 825 Fisher Street, Martinsville, Va., in 55 gallon drum and tanker load quantities.

The chelating agent GLC, which is sometimes referred to as gluconate and/or as sodium gluconate, can be purchased from Jungbunzlauer AG, St. Alben—Vorstadt 90, CH-4002, Basel, Switzerland. It can be purchased as a powdered concentrate in 25 kg bags and 1000 kg bags. Sodium gluconate is the sodium salt of gluconic acid, which can be produced by fermentation of glucose. It can be white to tan in color, granular to fine in particle size, very soluble in water, non-corrosive, non-toxic, and/or readily biodegradable (98% after 2 days).

Formulation of one liter of the ferric chelate Fe-GLC (sometimes referred to herein as VTXF) can be made by adding approximately 21.9 grams of GLC—Na3 of sodium gluconate to approximately 800 milliliters of water. This solution can be then mixed continuously with a magnetic stir bar or other mechanical mixing technique. Liquid ferric chloride solution can be added to the solution while the pH of the mixture is monitored. The pH of gluconate/water mixture can be adjusted to approximately 11 initially with sodium hydroxide. Ferric chloride then can be added until the pH of the solution comes down to a pH of approximately 4.0. The pH is readjusted to approximately 7.0 with sodium hydroxide to assure that all chelation sites are saturated with ferric ion. Water can be added to achieve a final volume of approximately 1000 millimeters. At this point the Fe-GLC can be ready for use at approximately 0.1M. Larger volumes can be produced by scaling-up this formulation. In certain exemplary embodiments, liquid ferric chloride solution can be added to approximately pH 11 GLC as a concentrated water/liquid mixture of approximately 30% sodium gluconate by weight to approximately 70% water followed by liquid ferric chloride addition (using an approximately 35% ferric chloride solution) to achieve a pH of the ferric gluconate solution of approximately 4.0 after the ferric chloride titration. The pH is readjusted to approximately 7.0 with sodium hydroxide to assure that all chelation sites are saturated with ferric ion.

The Fe-GLC can be applied to a contaminated medium before, during, in combination with, and/or after an oxidizing agent in amounts and/or concentrations effective to degrade, and/or substantially reduce the concentration of, the target contaminant. The amounts of Fe-GLC and oxidizing agent needed and/or utilized can depend upon, for example, the concentration of the contaminant(s) to be degraded, the available reaction time, temperature of the reactants (e.g., the Fe-GLC, the oxidizing agent, and/or the contaminated medium), and/or the organic matter content of the medium.

In certain exemplary embodiments, the Fe-GLC and the oxidizing agent can be mixed, and even conveyed, before being applied to the contaminated medium. In certain exemplary embodiments, the Fe-GLC and the oxidizing agent can mix while in contact with the contaminated medium.

At activity 1030, the Fe-GLC and the oxidizing agent can be applied to the contaminant, the medium, and/or the contaminated medium. Either of the Fe-GLC and the oxidizing agent can be applied as solid, liquid, vapor, aerosol, and/or foam.

For example, a ferric chelate and an oxidizing agent can contact the contaminated medium in the presence of water, such as in an aqueous soil slurry. In this context, the term "slurry" can mean a mixture containing sufficient water to moisten and saturate the soil and coat the soil particles, i.e., making "mud". In certain exemplary embodiments, sufficient water can be utilized to actually suspend the soil particles.

In certain exemplary embodiments involving soil, chelate and oxidizing agent solutions can be employed, and these can simply be added to the soil at ambient temperature, so long as there is sufficient water present in the final mud to allow penetration of the ingredients. Also, more concentrated oxidizing agent and chelate solutions can be mixed into soil that has been recently moistened or watered. Moreover, oxidizing agent and chelate can be sprayed on freshly plowed earth, and sunlight can speed degradation. In certain exemplary embodiments, ultra-violet light and/or other forms of light, radiation, and/or energy, etc., can be utilized to speed degradation.

At activity 1040, the reaction between the Fe-GLC, oxidizing agent, and the contaminant can be monitored, adjusted, and/or controlled. For example, included in this activity can be activities such as sampling the medium to detect if a contaminant is still present, analyzing the sample or the medium to identify what contaminant(s) remains and/or to determine what concentrations of the contaminant remain, and/or monitoring, adjusting, and/or controlling one or more operating parameters, e.g., temperatures, pressures, amounts, and/or flowrates of the contaminated medium, the Fe-GLC, the oxidizing agent, and/or the decontaminated medium.

To increase the temperature, pressure, and/or rate of the reaction, an accelerant can be added to, for example, the contaminated medium, the Fe-GLC, the oxidizing agent, and/or the reacting mixture. Such an accelerant can be, for example, an organic compound and/or biological that can react rapidly with the Fe-GLC and the oxidizing agent. Such an approach could be useful for fragmenting soil clods that contain a relatively low-level of contaminant, thereby increasing the available surface area of the soil and decreasing the time required to contact the contaminant with the other reactants, and/or decreasing the amount of Fe-GLC and/or oxidizing agent. Similarly, a non-toxic organic accelerant could be put into sub-surface groundwater to cause substantial bubbles to be formed during the reaction, thereby lifting the reactants and/or oxidants up to the soil/water interface where the target contaminants might be located.

During the reaction, at least a portion of the contaminant can be oxidized, decontaminated, and/or sanitized. In the case of biologicals, the reaction can kill a life form, render ineffective an amino acid, and/or denature a protein. The reaction can be particularly handy for decontaminating a cleanroom, sanitizing military equipment, and/or reducing a concentration of a contaminant associated with bio-terrorism. As a result of the reaction, the concentration of the contaminant can be reduced by a factor of, for example, at least 2, 5, 10, 20, 50, 100, 200, 500, 1000, 2000, 5000, 10000, 20000, and/or 50000, etc., and/or a factor between any of those values.

Heat generated by the reaction can be captured, transferred, and/or utilized. For example, the reaction can occur within a reactor vessel that is surrounded by cooling coils. The heat absorbed by a heat transfer fluid circulating in the coils can be used for any heating purpose, such as to dry the decontaminated medium (e.g., to de-water decontaminated soil and/or to dry a decontaminated surface), and/or to heat another process, fluid, and/or environment.

Moreover, the reaction can occur with such intensity as to create a controlled and/or uncontrolled explosion. A controlled explosion can be used, for example, to generate propulsion, and/or to create a mechanical cleaning effect. As a further example, the pressure, temperature, and/or decontamination caused by a sufficiently rapid reaction down-hole in an oil well can "frac" the well, thereby removing and/or dislodging substances clogging the well and improving a flowrate of the oil well.

The reaction can be allowed to run its course, and/or can be halted, for example, before complete oxidation of the contaminant has occurred. Adding an additional oxidizable substance to the medium, thereby diverting some of the reactants and/or oxidants to the additional substance and/or consuming the oxidants' oxidizing capability can cause such a halting. Moreover, such a halting of the reaction, or at least a decrease in the reaction rate, can also occur by reducing and/or limiting the flow of the reactants (e.g., either Fe-GLC, the oxidizing agent, the contaminated medium, and/or the additional oxidizable substance), changing the concentration of any of the reactants, lowering the temperature of any of the reactants, and/or by withdrawing heat generated by the reaction.

After the reaction, the medium can be treated to reduce a concentration of iron associated with the medium. The medium can also be re-treated to further reduce a concentration of the contaminant.

At activity 1050, the decontaminated medium can be disposed. Prior to disposal, however, the medium can be sampled to detect if any contaminant is still present, analyzed to identify what contaminant(s) remain, and/or to determine what concentrations of the contaminant are present. Further, a determination can be made regarding how much reduction has occurred in the target contaminant(s).

Also, the decontaminated medium can be conveyed to a disposal site, and can be discharged at the disposal site. The disposal site can be, for example, the atmosphere, a waterway, an injection well, and/or a landfill.

System 200

Figure 2:
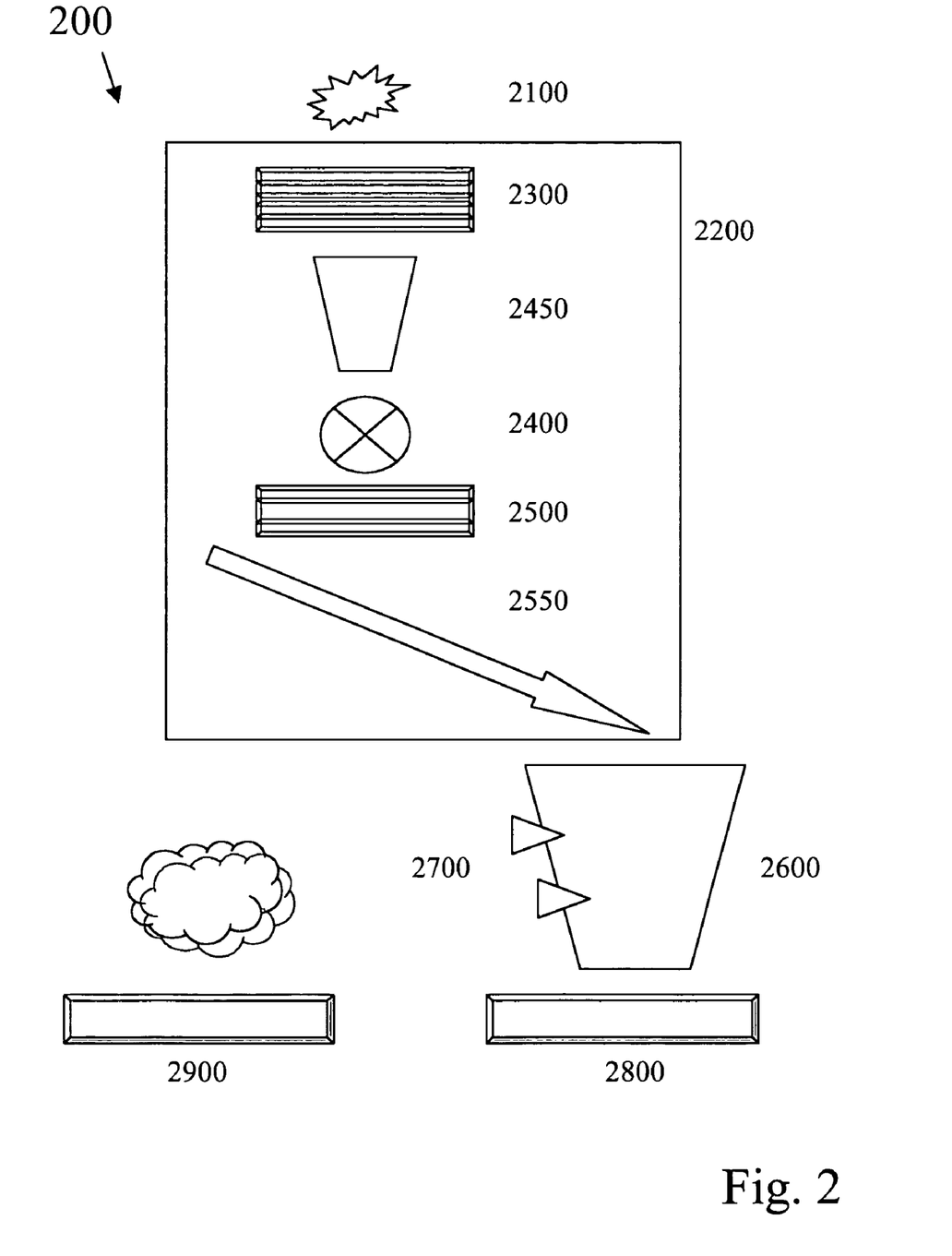
FIG. 2 is a block diagram of an exemplary embodiment of a system 200.

Certain exemplary embodiments can employ a system 200 for treating a contaminated medium.

Certain exemplary embodiments can be used for treating contaminated soil. In certain exemplary embodiments, each particle of contaminated soil can be saturated with both the oxidizing agent (hydrogen peroxide in this example) and Fe-GLC. Dose rates can vary with contaminant and background soil demand for the oxidants generated by the reactants.

Aliquots of contaminated soil can be exposed to varying levels of hydrogen peroxide and Fe-GLC. Once treated, the soil can be tested for the target contaminants to determine the efficacy of individual dose rates. Generally speaking, a dose rate of approximately 35% hydrogen peroxide for moderately contaminated soil (i.e. approximately 1000 ppm of target contaminant) will range from approximately 0.004% to approximately 0.012% by weight of hydrogen peroxide to soil. Fe-GLC can be added at the same weight to weight ratio as the hydrogen peroxide, when made up as an approximately 0.1 molar solution. Deviations from this range can be employed. For example, excessive moisture levels inherent within a target soil can suggest use of a more concentrated treatment solution that could decrease concerns for over-wetted soil.

Once the appropriate dosage of hydrogen peroxide and Fe-GLC are determined, the contaminated soil 2100 can be fed through a soil screening plant 2200. Soil screening plants are commonly available from a number of suppliers including Power Screen, Inc. and Extec, Inc. The soil screen can be equipped with a "grizzly" 2300 (a large vibrating grid of, for example, approximately 6" wide steel girders), for removing large debris from the soil and/or a hammermill/shredder 2400, and which can effectively reduce soil particle size to approximately one inch.

Soil can be loaded with a front end loader or backhoe onto the "grizzly" 2300, which can screen large debris from the soil. Soil can fall through the "grizzly" 2300 into a hopper 2450 where the hammermill/shredder 2400 can be located. Once pulverized with the hammermill/shredder 2400, the soil can fall onto a vibrating screen 2500 which can effectively reduce soil particle size to less than about one-half inch. Soil falling through the screen vibrating 2500 can land on a conveyor belt 2550 where it can be transported to the exit point of the screening plant.

As the soil free falls from the conveyor system 2550 it can fall through a shroud 2600. Inside of the shroud 2600 can be located numerous (e.g., approximately 32) individual spray nozzles 2700 which can deliver the prescribed dosage of hydrogen peroxide and Fe-GLC. Each product can be sprayed separately through a dedicated bank of nozzles 2700 for each product. Nozzles 2700 within the shroud 2600 can be placed in a pattern, such as a circular or helical pattern. Soil can fall through the pattern of nozzles 2700 so that the soil can be spayed from numerous angles. Fe-GLC can be sprayed first followed immediately by the hydrogen peroxide. Control of the spray volume to soil ratio can be controlled by knowing the soil processing rate through the equipment and matching this rate to predetermined volumes being sprayed onto the soil as can be indicated by totalizing flow controls for each fluid.

Soil exiting the treatment unit can fall into a lined pit 2800 where the soil can be excavated with rubber-tired loaders and placed into a final treatment cell 2900 for finalized oxidation, cooling, and/or dewatering. Soil can be tested after a predetermined time, (e.g., about three hours) for cleanliness.

Alternatively methods for applying the chemicals to soil are contemplated. For example, a pug mill could be used to mix the chemicals into the soil via an auger arrangement. As another example, one could simply spray the chemicals onto the soil and mix them in with heavy equipment such as a backhoe, or even simply roto-till them into the soil.

The degradation reaction employed in certain exemplary embodiments can occur at the pH of the soil, which can range from approximately 3.5 to approximately 8, or from approximately 5 to approximately 7, or more typically approximately 6. Usually, no acidification of the slurry is required, and typically, degradation can occur even where the soil buffers the reaction.

Certain exemplary embodiments can be used to reduce contaminants associated with surfaces, solids, water, air, and/or fluids generally. Certain exemplary embodiments can cause insignificant sludge production, can work on cloudy effluents, and/or can work at circumneutral pH. For certain exemplary embodiments, the Fe-GLC and/or oxidizing agent can be in any fluid form, including liquid, vapor, foam, and/or aerosol form.

Certain exemplary embodiments can be implemented as stand-alone systems, combined with each other, and/or with pre-treatment processes such as bioremediation and/or solids separation. Certain exemplary embodiments can be fully integrated, self-contained, skid-mounted, portable, weatherproof, tolerant of suspended dissolved solids and color, highly energy efficient, remotely monitored, equipped with 100 percent duplicity of all components, and/or fully automatically PLC controlled. Certain exemplary embodiments have built-in heating; venting; sump; digital operator interface; and/or flow, concentration, pH, temperature, and/or pressure instrumentation and/or controls.

EXAMPLE 1

Bench Treatment Water Treatment Using Fe-GLC

Table 2 shows pre-treatment and post-treatment concentrations (in parts per million) of numerous contaminants in water, the contaminated water treated according to certain exemplary embodiments. Each of the contaminants was dissolved in separate flasks containing one liters of water. Each of the flasks was treated with 1.0 ml of Fe-GLC (0.1M) and 1.0 ml of 35% hydrogen peroxide.

TABLE 2

| Contaminant | CAS # | Before Treatment (ppm) | After Treatment (ppm) |
|---|---|---|---|
| Benzene | 71-43-2 | 110.0 | ND* |
| Toluene | 108-88-3 | 121.3 | ND |
| Trichloroethane | 79-01-6 | 354.2 | ND |
| Tetrachloroethane | 127-16-4 | 136.2 | 24.3 |
| Ethylbenzene | 100-41-4 | 80.3 | ND |
| Hydrogen Sulfide | 7783-06-4 | 100.0 | ND |

*Note: ND indicates non-detectible.

EXAMPLE 2

A Comparative Treatment of 2,4-Dichlorophenoxyacetic Acid (2,4-D) with Hydrogen Peroxide Alone Against Hydrogen Peroxide/Fe-Gluconate A solution containing 1.5 L of distilled water, approximately 0.2 g of sodium bicarbonate, and a small amount of sodium salt of 2,4-D were prepared with magnetic stirring at room temperature in a 2.5 L flask. The dissolved sodium bicarbonate increased the alkalinity of the water somewhat, causing the water to mimic a natural water source. Two hundred fifty milliliters of this solution was distributed into three 500 mL Erlenmeyer flasks. Flask one served as a control and had no Fe-GLC or hydrogen peroxide added to it and was labeled "untreated". Two hundred microliters of 50% hydrogen peroxide was added to flask two and the flask was labeled "oxidizing agent only". Flask three received 200 microliters of 50% hydrogen peroxide and 200 microliters of Fe-GLC and was labeled "Treated w/oxidizing agent and VTXF".

The flasks were then covered with parafilm and swirled to facilitate mixing of the solution. After four hours a sample from each flask was taken to the pesticide lab at Virginia Tech and analyzed by gas chromatography (GC) for 2,4-D. The findings were as follows:

TABLE 3

Results of 2,4-D Treatments Comparing H2O2 and H2O2 with Fe-GLC

| Sample Description | Lab ID# | 2,4-D |
|---|---|---|
| Untreated | S-O 4001 | 130 ppb |
| Oxidizing agent Only | S-O 4002 | 230 ppb |
| Treated w oxidizing agent & VTXF | S-O 4003 | 2.5 ppb |
| Rinsate sample 1 | N/A | 0.08 ppb |
| Rinsate sample 2 | N/A | 0.02 ppb |
| Rinsate sample 3 | N/A | 0.01 ppb |

Results indicate that the hydrogen peroxide had no affect on the 2,4-D when added alone. However, hydrogen peroxide along with the Fe-GLC (VTXF) catalyst substantially reduced the concentration of the 2,4-D, indicating that the catalyzed process was a much more vigorous oxidative process than hydrogen peroxide alone.

EXAMPLE 3

Treatment of Groundwater Contaminated with BTEX and MtBE Using Hydrogen Peroxide Alone and Hydrogen Peroxide with Fe-GLC A groundwater sample known to contain benzene, toluene, ethylbenzene, xylenes and methyl tert-butyl ether (MtBE) was divided into three separate 250 milliliter aliquots and placed into 500 milliliter beakers. Nothing was added to beaker one, one milliliter of 35% hydrogen peroxide was added to the second beaker and one milliliter of 35% hydrogen peroxide along with 1 milliliter of Fe-GLC was added to the third beaker. Each sample was stirred gently with a glass stirring rod to assure mixture of the liquids with the sample. The samples were poured into individual sample containers and taken to the laboratory for analysis. The findings were as follows:

TABLE 4

Results of BTEX/MtBE Treatments Comparing H2O2 Alone Against H2O2 and Fe-GLC

| Analysis BTEX SW 846 8260 | Untreated (ppb) | H2O2 Only (ppb) | H2O2 w/Fe-GLC (ppb) |
|---|---|---|---|
| Benzene | 56 | 15.1 | ND |
| Ethylbenzene | 34 | 13.0 | ND |
| Toluene | 171 | 55.7 | ND |
| Xylenes | 159 | 67.0 | ND |
| MtBE | 27 | 15.7 | 1.8 |

ND = non detectible

The results indicate that the hydrogen peroxide/Fe-GLC mixture was a more effective method for degrading the target compounds.

EXAMPLE 4

Comparison of Peroxide Alone to Fe-GLC and Peroxide for Disinfecting Wastewater A sample of wastewater was collected from the influent of the chlorine contact chamber of the York River Wastewater Treatment Plant in Yorktown, Va. The samples were divided equally into three clean 500 milliliter sample containers from the single sample taken. The first sample served as a control and was set aside. Twenty milligrams of hydrogen peroxide was added to the second sample (50 microliters of 35% hydrogen peroxide). Twenty milligrams of hydrogen peroxide (50 microliters of 35% H2O2) was added to the third container along with 50 microliters of Fe-GLC. Each sample was capped and shaken briefly to mix the contents. After twenty minutes, sub-samples were taken from each vessel and pored into fecal coliform sample containers for analysis at the Hampton Roads Sanitary District lab. The findings were as follows:

TABLE 5

Bacterial Disinfection Using Fe-GLC

| Sample ID | Sample Date | Fecal Coliform* #cfu/100 mL |
|---|---|---|
| Control | Nov. 13, 2003 | 2200 |
| H2O2 Only | Nov. 13, 2003 | 53 |
| H2O2/FeGLC | Nov. 13, 2003 | <1 |

*cfu = colony forming units

Results indicate that the VTXF sample was more effective in disinfecting the treated municipal wastewater. Fifty three CFUs/100 mls remained in the hydrogen peroxide only test while no detectable CFUs were indicated in the VTXF sample. Both treatments reduced fecal coliforms substantially from the control.

EXAMPLE 5

Disinfection of Wastewater Using a Variety of Chelated Iron Compounds

Wastewater collected from the aeration basin of the County of Spotsylvania, Virginia's Massaponax Wastewater Treatment Plant was treated with hydrogen peroxide alone and separately with a combination of hydrogen peroxide and a variety of individual chelated iron products, to assess the difference, if any, between the disinfection capabilities of hydrogen peroxide alone against hydrogen peroxide catalyzed with the various chelated iron products.

If the chelated iron products are capable of producing hydroxyl radicals in the presence of hydrogen peroxide, it is believed that a marked improvement will be noted between those samples treated with peroxide alone and those with hydrogen peroxide plus a chelated iron product.

A 10 gallon sample of wastewater from the Massaponax Wastewater Plant was collected and allowed to sit undisturbed for thirty minutes. The clarified supernatant was then pored off of the top of the settled solids within the sample. The supernatant was then mixed and four samples were collected to determine untreated heterotrophic bacteria counts.

The four chelants selected were as follows:

1. HEIDA (N-2(2-hydroxyethyliminodiacetic acid)

2. EDTA (ethylenediaminetetracetic acid)

3. NTA (nitrilotriacetic acid)

4. Gluconic Acid

Chelants were dissolved in distilled water at 0.4334M. Ferric chloride was added in amounts to achieve saturation of chelant sites on the respective chelants. This was achieved by adding ferric chloride until a pH of 4 was achieved and then titrating each chelant-iron mixture with sodium hydroxide until a pH of 7 was achieved. Iron oxide precipitate was noted in each sample as the pH rose, indicating saturation of the chelated sites had occurred for each chelant.

Twenty individual liter samples of supernatant were then decanted from the well-mixed wastewater sample for testing. Four chelated iron products with peroxide were tested at two test concentrations and compared to samples receiving peroxide only and iron chelate only. In Test 1, each of four liter test containers received a dose of 6 ppm of one of the iron chelates plus 19.8 ppm of hydrogen peroxide. Four additional four liter test containers received 19.8 ppm of hydrogen peroxide alone. In Test 2, this protocol was repeated with additional four liter test containers with twice the concentrations of each additive (i.e., 12 ppm iron chelant and 39.6 ppm hydrogen peroxide). Finally, in Test 3, each of four liter samples received a dosage of 12 ppm of iron chelant alone to test the effect, if any, of the chelant.

Individual samples were dosed with the respective additives, mixed with a magnetic stir bar and allowed to react for 30 minutes. Samples were then decanted to sterile sample containers containing sodium thiosulfate to stop the oxidation process and preserve the sample. Samples were then placed in a refrigerator until all samples were finished. Samples were packaged in a standard cooler with ice packs and sent via overnite delivery to ProChem Labs in Lynchburg, Va. for analysis for total heterotrophic bacteria counts.

Raw samples were reported to contain 17,600, 17,350, 16,200 and 21,600 colony forming units/ml (CFUs) for an average of 18,188 CFUs. Treated samples resulted in the data presented below:

TABLE 6

Bacterial Disinfection Using Chelated Iron Compounds

| Iron Chelant | Test 1 CFUs/ml | | Test 2 CFUs/ml | | Test 3 CFUs/ml |
|---|---|---|---|---|---|
| | 19.8 ppm $H_2O_2$ Only | 19.8 ppm $H_2O_2$ 6 ppm Fe-Chelant | 39.6 ppm $H_2O_2$ Only | 39.6 ppm $H_2O_2$ 12 ppm Fe-Chelant | 12 ppm Fe-Chelant |
| Fe-EDTA | 340 | 360 | 49 | 59 | 18,200 |
| Fe-HEIDA | 1070 | 1350 | 35 | 84 | 16,700 |
| Fe-NTA | 480 | 370 | 68 | 75 | 18,300 |
| Fe-GLU | 840 | 98 | 330 | 28 | 22,600 |

Table 6 indicates that the hydrogen peroxide alone is a good disinfectant. From these data it is possible to say that Fe-EDTA, Fe-HEIDA and Fe-NTA had very little effect on viable cells beyond that exhibited by hydrogen peroxide alone. However, it appeared that the disinfection in the samples receiving ferric gluconate (Fe-GLU) and peroxide were better than peroxide alone, particularly in the case of the lower dosage rate. It is more difficult to make an assessment in Test 2 for Fe-GLU because of the elevated peroxide-only test sample which was considerably higher than the other three peroxide-only samples in this test. However, the test results were improved for the Fe-GLU as compared to the other three ferric chelants plus peroxide tests.

Test 3, which received ferric chelants only, approximated the raw sample test results. Average results for this test was 18,950 CFUs/ml as compared to 18,188 CFUs/ml for the raw untreated sample average.

EXAMPLE 6

Treatment of Sulfides in Municipal Wastewater Using a Variety of Ferric Chelants and Hydrogen Peroxide A variety of ferric chelants in combination with hydrogen peroxide were tested to determine their impact on the efficiency of treatment of sulfide in wastewater compared to samples of wastewater treated with hydrogen peroxide only. It has been demonstrated in a previous study presented herein that a combination of ferric gluconate and hydrogen peroxide was very effective in reducing the concentration of sulfide within a test sample. However, since it is known that hydrogen peroxide will treat sulfide without the aid of a ferric chelant, it was decided to conduct studies with ferric gluconate and a variety of other ferric chelants to determine if an improvement to the efficiency of treatment within 30 minutes could be accomplished above and beyond what could be achieved with hydrogen peroxide alone.

Seven chelants were chosen for the study as follows:
1. HEIDA (N-2(2-hydroxyethyliminodiacetic acid)
2. EDTA (ethylenediaminetetracetic acid)
3. NTA (nitrilotriacetic acid)
4. Gluconic acid
5. Gallic acid
6. Ascorbic acid
7. Citric acid Chelants 1 through 3 represent the class of chelants known as the aminopolycarboxylates, gallic acid is a polyhydroxyaromatic, citric and ascorbic acid are classed as polycarboxylates and gluconic acid is sugar acid (aldonic acid). It was determined that a broad sampling of chelants from several different classes could determine if the production of oxidants and/or hydroxyl radicals from mixtures of ferric chelants and oxidizing agents was more likely to be an individual chemical phenomena or a chemical class phenomena.

Formulations of the various ferric chelants was accomplished by adding 35% ferric chloride to 0.3 Molar solutions of each chelant. Solutions of HEIDA, EDTA, and NTA, each of which had a high pH, were made by adding the appropriate amount of ferric chloride to the chelants to achieve saturation of available sites on the molecules. Since each of these three chelants had a starting pH of 11, 35% ferric chloride was added until a pH of 4 was attained. The pH was then raised to 7 using sodium hydroxide. Precipitation of iron oxides and/or hydroxides at this pH offered assurance of complete chelation of still soluble iron after 24 hours.

Gluconic, citric, and ascorbic acids were made by adding sodium hydroxide to 0.3 M solutions of each of the solutions until a pH of 11 was attained. The pH was then lowered to 4 as with the aminopolycarboxylates using 35% ferric chloride and then returned to pH 7 with sodium hydroxide to assure saturation of all chelation sites with ferric ions (Fe oxide precipitate noted after 24 hours).

Gallic acid is less soluble than all of the other chelants and was made up at 0.014 M to accommodate its solubility. The pH of gallic acid was adjusted to 11 as well. The pH was then lowered to 4 as with the aminopolycarboxylates using 35% ferric chloride and then returned to pH 7 with sodium hydroxide to assure saturation of all chelation sites with ferric ions (Fe oxide precipitate noted after 24 hours).

Total sulfides were tested for using Standard Methods 4500-$S^{2-}$ D with a Hach Chemical Company (of Loveland, Colo.) DR 2000 Spectrophotometer and reagents from Hach specific for this particular test. To keep total sulfides within the range of the test, samples were diluted with distilled water prior to conducting the test as per Hach instructions.

For testing Series One, a batch of raw influent wastewater from a local wastewater plant was spiked with sulfide to attain a final total sulfide concentration of 25.4 ppm (average of three samples taken of 26.3, 25.4, and 24.6 ppm). Each of the seven liter sample jars of the raw wastewater received a dose of 12 ppm of one of the seven ferric chelants (mass calculated as chelant) and 37.8 ppm of hydrogen peroxide on a staggered schedule to accommodate testing time. The 37.8 ppm of hydrogen peroxide represented a ratio of ~1.5:1 of peroxide to sulfide. Tests for total sulfide were conducted after 5, 15, and 30 minutes of contact time on each of the seven liter test jars. A second set of seven liter jars of wastewater was conducted using 37.8 ppm of hydrogen peroxide and 6 ppm of ferric chelants and tested on the same schedule as before. A third set of seven liter jars of wastewater was tested using 37.8 ppm of hydrogen peroxide dosing alone for each of seven vessels and tested over time as before. Finally, seven individual liter vessels received dosages of the ferric chelants only and were tested after 30 minutes to determine if the chelants alone had an effect on sulfide.

The tests resulted in the following tabulated data:

TABLE 7

Series One Studies - 1.5:1.0 Peroxide to Sulfide Ratio and Two Chelate Dosages
Ferric EDTA Study*

| Contact Time (Minutes) | Sulfide Remaining (ppm) | | | |
|---|---|---|---|---|
| | Dose 1 12 ppm Chelant | Dose 2 6 ppm Chelant | Dose 3 $H_2O_2$ Only | Dose 4 Chelant Only |
| 0 | 25.4 | 25.4 | 25.4 | 25.4 |
| 5 | 18.3 | 18.6 | 18.6 | |
| 15 | 9.9 | 12.8 | 15.3 | |
| 30 | 8.0 | 9.1 | 11.3 | 24.4 |

*Hydrogen peroxide at 37.8 ppm for all Doses except Dose 4.

TABLE 8

Series One Studies - 1.5:1.0 Peroxide to Sulfide Ratio and Two Chelate Dosages
Ferric NTA Study*

| Contact Time (Minutes) | Sulfide Remaining (ppm) | | | |
|---|---|---|---|---|
| | Dose 1 12 ppm Chelant | Dose 2 6 ppm Chelant | Dose 3 $H_2O_2$ Only | Dose 4 Chelant Only |
| 0 | 25.4 | 25.4 | 25.4 | 25.4 |
| 5 | 15.2 | 15.9 | 17.9 | |
| 15 | 6.8 | 12.6 | 13.8 | |
| 30 | 5.5 | 7.9 | 10.4 | 24.6 |

*Hydrogen peroxide at 37.8 ppm for all Doses except Dose 4.

TABLE 9

Series One Studies - 1.5:1.0 Peroxide to Sulfide Ratio and Two Chelate Dosages
Ferric HEIDA Study*

| Contact Time (Minutes) | Sulfide Remaining (ppm) | | | |
|---|---|---|---|---|
| | Dose 1 12 ppm Chelant | Dose 2 6 ppm Chelant | Dose 3 $H_2O_2$ Only | Dose 4 Chelant Only |
| 0 | 25.4 | 25.4 | 25.4 | 25.4 |
| 5 | 20.0 | 20.3 | 20.0 | |

TABLE 9-continued

Series One Studies - 1.5:1.0 Peroxide to Sulfide Ratio and Two Chelate Dosages
Ferric HEIDA Study*

| Contact Time (Minutes) | Sulfide Remaining (ppm) | | | |
| --- | --- | --- | --- | --- |
| | Dose 1 12 ppm Chelant | Dose 2 6 ppm Chelant | Dose 3 $H_2O_2$ Only | Dose 4 Chelant Only |
| 15 | 16.5 | 16.4 | 14.4 | |
| 30 | 14.2 | 14.9 | 13.6 | 25.2 |

*Hydrogen peroxide at 37.8 ppm for all Doses except Dose 4.

TABLE 10

Series One Studies - 1.5:1.0 Peroxide to Sulfide Ratio and Two Chelate Dosages
Ferric Gluconate Study*

| Contact Time (Minutes) | Sulfide Remaining (ppm) | | | |
| --- | --- | --- | --- | --- |
| | Dose 1 12 ppm Chelant | Dose 2 6 ppm Chelant | Dose 3 $H_2O_2$ Only | Dose 4 Chelant Only |
| 0 | 25.4 | 25.4 | 25.4 | 25.4 |
| 5 | 14.2 | 15.9 | 20.2 | |
| 15 | 7.3 | 11.5 | 14.8 | |
| 30 | 4.3 | 7.4 | 11.1 | 24.9 |

*Hydrogen peroxide at 37.8 ppm for all Doses except Dose 4.

TABLE 11

Series One Studies - 1.5:1.0 Peroxide to Sulfide Ratio and Two Chelate Dosages
Ferric Gallate Study*

| Contact Time (Minutes) | Sulfide Remaining (ppm) | | | |
| --- | --- | --- | --- | --- |
| | Dose 1 12 ppm Chelant | Dose 2 6 ppm Chelant | Dose 3 $H_2O_2$ Only | Dose 4 Chelant Only |
| 0 | 25.4 | 25.4 | 25.4 | 25.4 |
| 5 | 18.4 | 18.0 | 18.1 | |
| 15 | 14.0 | 13.6 | 13.9 | |
| 30 | 10.4 | 11.2 | 10.9 | 24.7 |

*Hydrogen peroxide at 37.8 ppm for all Doses except Dose 4.

TABLE 12

Series One Studies - 1.5:1.0 Peroxide to Sulfide Ratio and Two Chelate Dosages
Ferric Citrate Study*

| Contact Time (Minutes) | Sulfide Remaining (ppm) | | | |
| --- | --- | --- | --- | --- |
| | Dose 1 12 ppm Chelant | Dose 2 6 ppm Chelant | Dose 3 $H_2O_2$ Only | Dose 4 Chelant Only |
| 0 | 25.4 | 25.4 | 25.4 | 25.4 |
| 5 | 17.8 | 18.1 | 18.9 | |
| 15 | 14.1 | 15.8 | 15.8 | |
| 30 | 10.5 | 12.4 | 11.3 | 25.0 |

*Hydrogen peroxide at 37.8 ppm for all Doses except Dose 4.

TABLE 13

Series One Studies - 1.5:1.0 Peroxide to Sulfide Ratio and Two Chelate Dosages
Ferric Ascorbate Study*

| Contact Time (Minutes) | Sulfide Remaining (ppm) | | | |
| --- | --- | --- | --- | --- |
| | Dose 1 12 ppm Chelant | Dose 2 6 ppm Chelant | Dose 3 $H_2O_2$ Only | Dose 4 Chelant Only |
| 0 | 25.4 | 25.4 | 25.4 | 25.4 |
| 5 | 16.6 | 17.2 | 17.8 | |
| 15 | 11.8 | 12.4 | 14.2 | |
| 30 | 9.6 | 10.4 | 11.5 | 24.6 |

*Hydrogen peroxide at 37.8 ppm for all Doses except Dose 4.

For testing Series Two, a second batch of raw influent wastewater from the same local wastewater plant was spiked with sulfide to attain a total sulfide concentration of 42.3 ppm (average of three samples taken of 42.7, 40.6, and 43.5 ppm). Each of seven liter sample jars of the raw wastewater received a dose of 20 ppm of one of the seven ferric chelants (mass calculated as chelant) and 105.8 ppm of hydrogen peroxide on a staggered schedule to accommodate testing time. The 105.8 ppm of hydrogen peroxide represented a ratio of ~2.5:1 of peroxide to sulfide. Tests for total sulfide were conducted after 5, 15, and 30 minutes of contact time on each of the seven liter test jars. A second set of seven liter jars of wastewater was tested using 105.8 ppm of hydrogen peroxide and 10 ppm of ferric chelants and tested on the same schedule as before. A third set of seven liter jars of wastewater was tested using 105.8 ppm of hydrogen peroxide dosing alone for each of seven vessels and tested over time as before. Finally, seven individual liter vessels received dosages of the ferric chelants only at 20 ppm and were tested after 30 minutes to determine if the chelants alone had an effect on sulfide.

TABLE 14

Series Two Studies - 2.5:1.0 Peroxide to Sulfide Ratio and Two Chelate Dosages
Ferric EDTA Study*

| Contact Time (Minutes) | Sulfide Remaining (ppm) | | | |
| --- | --- | --- | --- | --- |
| | Dose 1 20 ppm Chelant | Dose 2 10 ppm Chelant | Dose 3 $H_2O_2$ Only | Dose 4 Chelant Only |
| 0 | 42.3 | 42.3 | 42.3 | 42.3 |
| 5 | 25.8 | 27.4 | 29.4 | |
| 15 | 16.9 | 18.9 | 20.3 | |
| 30 | 5.3 | 6.9 | 13.1 | 41.7 |

*Hydrogen peroxide at 105.8 ppm for all Doses except Dose 4.

TABLE 15

Series Two Studies - 2.5:1.0 Peroxide to Sulfide Ratio and Two Chelate Dosages
Ferric NTA Study*

| Contact Time (Minutes) | Sulfide Remaining (ppm) | | | |
| --- | --- | --- | --- | --- |
| | Dose 1 20 ppm Chelant | Dose 2 10 ppm Chelant | Dose 3 $H_2O_2$ Only | Dose 4 Chelant Only |
| 0 | 42.3 | 42.3 | 42.3 | 42.3 |
| 5 | 23.3 | 26.7 | 29.4 | |
| 15 | 12.6 | 16.3 | 21.2 | |
| 30 | 2.8 | 4.2 | 12.9 | 41.0 |

*Hydrogen peroxide at 105.8 ppm for all Doses except Dose 4.

TABLE 16

Series Two Studies - 2.5:1.0 Peroxide to Sulfide Ratio and Two Chelate Dosages
Ferric HEIDA Study*

| Contact Time (Minutes) | Sulfide Remaining (ppm) | | | |
|---|---|---|---|---|
| | Dose 1 20 ppm Chelant | Dose 2 10 ppm Chelant | Dose 3 $H_2O_2$ Only | Dose 4 Chelant Only |
| 0 | 42.3 | 42.3 | 42.3 | 42.3 |
| 5 | 25.3 | 27.1 | 30.6 | |
| 15 | 19.8 | 18.9 | 20.1 | |
| 30 | 12.9 | 14.0 | 13.6 | 41.5 |

*Hydrogen peroxide at 105.8 ppm for all Doses except Dose 4.

TABLE 17

Series Two Studies - 2.5:1.0 Peroxide to Sulfide Ratio and Two Chelate Dosages
Ferric Gluconate Study*

| Contact Time (Minutes) | Sulfide Remaining (ppm) | | | |
|---|---|---|---|---|
| | Dose 1 20 ppm Chelant | Dose 2 10 ppm Chelant | Dose 3 $H_2O_2$ Only | Dose 4 Chelant Only |
| 0 | 42.3 | 42.3 | 42.3 | 42.3 |
| 5 | 18.6 | 23.5 | 29.3 | |
| 15 | 5.6 | 7.3 | 19.4 | |
| 30 | 1.1 | 2.2 | 14.2 | 43.0 |

*Hydrogen peroxide at 105.8 ppm for all Doses except Dose 4.

TABLE 18

Series Two Studies - 2.5:1.0 Peroxide to Sulfide Ratio and Two Chelate Dosages
Ferric Gallate Study*

| Contact Time (Minutes) | Sulfide Remaining (ppm) | | | |
|---|---|---|---|---|
| | Dose 1 20 ppm Chelant | Dose 2 10 ppm Chelant | Dose 3 $H_2O_2$ Only | Dose 4 Chelant Only |
| 0 | 42.3 | 42.3 | 42.3 | 42.3 |
| 5 | 29.2 | 27.8 | 29.4 | |
| 15 | 20.2 | 22.2 | 22.0 | |
| 30 | 13.2 | 13.1 | 14.2 | 43.0 |

*Hydrogen peroxide at 105.8 ppm for all Doses except Dose 4.

TABLE 19

Series Two Studies - 2.5:1.0 Peroxide to Sulfide Ratio and Two Chelate Dosages
Ferric Citrate Study*

| Contact Time (Minutes) | Sulfide Remaining (ppm) | | | |
|---|---|---|---|---|
| | Dose 1 20 ppm Chelant | Dose 2 10 ppm Chelant | Dose 3 $H_2O_2$ Only | Dose 4 Chelant Only |
| 0 | 42.3 | 42.3 | 42.3 | 42.3 |
| 5 | 30.1 | 29.9 | 28.9 | |
| 15 | 19.6 | 20.2 | 20.2 | |
| 30 | 14.3 | 12.9 | 13.0 | 42.0 |

*Hydrogen peroxide at 105.8 ppm for all Doses except Dose 4.

TABLE 20

Series Two Studies - 2.5:1.0 Peroxide to Sulfide Ratio and Two Chelate Dosages
Ferric Ascorbate Study*

| Contact Time (Minutes) | Sulfide Remaining (ppm) | | | |
|---|---|---|---|---|
| | Dose 1 20 ppm Chelant | Dose 2 10 ppm Chelant | Dose 3 $H_2O_2$ Only | Dose 4 Chelant Only |
| 0 | 42.3 | 42.3 | 42.3 | 42.3 |
| 5 | 26.9 | 27.2 | 30.1 | |
| 15 | 17.7 | 19.7 | 21.2 | |
| 30 | 10.8 | 11.9 | 12.6 | 41.8 |

*Hydrogen peroxide at 105.8 ppm for all Doses except Dose 4.

Calculations of the percentage of sulfide treated after 30 minutes of contact were performed to assess the efficacy of the ferric chelates as compared to hydrogen peroxide treatments alone. These data follow:

TABLE 21

Percentage of Sulfide Treated After 30 Minutes - 1.5:1.0 Ratio of Peroxide to Sulfide

| | Percentage of Sulfide Treated | | |
|---|---|---|---|
| Fe Chelant | Dose 1 12 ppm Chelant 37.8 ppm $H_2O_2$ | Dose 2 6 ppm Chelant 37.8 ppm $H_2O_2$ | Dose 3 38.7 ppm $H_2O_2$ Only |
| Fe EDTA | 68.5 | 64.2 | 55.5 |
| Fe NTA | 78.3 | 68.9 | 59.0 |
| Fe HEIDA | 44.1 | 41.3 | 46.5 |
| Fe Gluconate | 83.1 | 70.8 | 56.3 |
| Fe Gallate | 59.1 | 55.9 | 57.0 |
| Fe Citrate | 58.7 | 51.2 | 55.5 |
| Fe Ascorbate | 62.2 | 59.0 | 54.7 |

TABLE 22

Percentage of Sulfide Treated After 30 Minutes - 2.5:1.0 Ratio of Peroxide to Sulfide

| Fe Chelant | Dose 1 20 ppm Chelant 105.8 ppm $H_2O_2$ | Dose 2 10 ppm Chelant 105.8 ppm $H_2O_2$ | Dose 3 105.8 ppm $H_2O_2$ Only |
|---|---|---|---|
| Fe EDTA | 87.5 | 83.7 | 69.0 |
| Fe NTA | 93.4 | 90.0 | 69.5 |
| Fe HEIDA | 69.5 | 66.9 | 67.8 |
| Fe Gluconate | 97.4 | 94.8 | 66.4 |
| Fe Gallate | 68.7 | 69.0 | 44.4 |
| Fe Citrate | 66.2 | 69.5 | 69.3 |
| Fe Ascorbate | 74.5 | 71.9 | 70.2 |

It is apparent from these data that three ferric chelates stand out from the seven tested. Ferrics EDTA, NTA, and Gluconate were noticeably better over 30 minutes of treatment than hydrogen peroxide alone. Also, there was no significant treatment noted within the ferric chelates alone indicating that the treatment of sulfide within wastewater was substantially improved in the ferric chelate and peroxide combination for these three ferric chelates.

Ferric HEIDA, which is within the family aminopolycarboxylate, did not perform well as compared to Ferric EDTA and NTA alone which suggests that the treatment efficacy may not be related to families of similar chemistry.

Ferric gallate and ascorbate did not perform well overall, although ferric ascorbate did show some modest improvement over hydrogen peroxide treatment alone.

The rate of treatment was also improved for samples receiving Ferrics EDTA, NTA, and Gluconate. After 15 minutes, hydrogen peroxide alone averaged 52% sulfide reduction in the 2.5:1.0 peroxide to sulfide treatments as compared to 60%, 70.2%, and 86.8% reduction, respectively, for the 20 ppm of Fe EDTA, Fe NTA, and Fe Gluconate and 105.8 ppm hydrogen peroxide treatments. Improved rates were also noted in the lower treatment level of 12 ppm chelant and 37.8 ppm hydrogen peroxide. Respective sulfide treatment for Fe EDTA, Fe NTA, and Fe Gluconate were 61%, 73%, and 70% as compared to 42.9% for peroxide alone. All of the other ferric chelants approximated the treatment rates of hydrogen peroxide alone.

It is concluded from this example that:
1. Ferric EDTA, ferric NTA, and ferric Gluconate significantly improve the overall efficiency of sulfide treatment after 30 minutes of treatment over peroxide alone.
2. Ferric EDTA, ferric NTA, and ferric Gluconate significantly improve the rate of treatment of sulfide over hydrogen peroxide alone.
3. The efficacy of sulfide treatment is chelant specific and is not necessarily tied to classes of chelants. Therefore, success in treatment is unique to selected, individual ferric chelants.
4. Higher concentrations of ferric EDTA, ferric NTA, and ferric Gluconate in combination with higher concentrations of hydrogen peroxide improves both overall efficiency of treatment and the rate of treatment.

EXAMPLE 7

Treatment of Sulfides in Municipal Wastewater Using a Variety of Ferric Chelants and Ozone A variety of ferric chelants in combination with ozone were tested to determine their impact on the efficiency of treatment of sulfide in wastewater over samples of wastewater receiving ozone only. Previous studies presented herein demonstrated that certain combinations of ferric chelants and hydrogen peroxide were very effective in reducing the concentration of sulfide within a test sample. However, since it is known that ozone alone will treat sulfide without the aid of selected ferric chelants, tests were conducted using four ferric chelants which have demonstrated varying degrees of effectiveness for improving the oxidation of sulfides in the presence of hydrogen peroxide.

The four ferric chelants chosen for the study were as follows:

1. HEIDA (N-2(2-hydroxyethyliminodiacetic acid)

2. EDTA (ethylenediaminetetracetic acid)

3. NTA (nitrilotriacetic acid)

4. Gluconic acid

Chelants 1 through 3 represent the class of chelants known as the aminopolycarboxylates and gluconic acid is sugar acid (aldonic acid).

It is hypothesized that those samples receiving ferric chelants will react with some amount of the ozone to produce hydroxyl radicals. It is further hypothesized that one, two and, possibly, three hydroxyl radicals can be produced from a single ozone molecule. The production of hydroxyl radicals in excess will improve the efficiency of treatment. The following reactions are pertinent to this study:

Ozone alone with sulfide:

$$S^= + 3O_3 \rightarrow SO_3^= + 3O_2 \qquad \text{(Equation 2)}$$

Theoretical hydroxyl radical formation from ozone and ferric chelates:

$$\text{Chelate} + O_3 \rightarrow 3O^- + 3H^+ \rightarrow 3OH\text{—} \qquad \text{(Equation 3)}$$

Other variations could involve the formation of single hydroxyl radicals and elemental oxygen or two hydroxyl radicals and a hydroxide ion or water molecule.

Hydroxyl radicals in a reaction with sulfide:

$$S^= + 2OH\text{—} \rightarrow S(\text{elemental sulfur}) \qquad \text{(Equation 4)}$$

Proof of this reaction to elemental sulfur was not done using test equipment, however, a heavy yellow precipitate was formed when ferric gluconate was added along with hydrogen peroxide into a solution containing over 1000 ppm of sulfide in a separate experiment. The yellow precipitate was indicative of the presence of elemental sulfur.

Formulations of the various ferric chelants was accomplished by adding 35% ferric chloride to 1.0 Molar solutions of each chelant. Solutions of HEIDA (samples from The Dow Chemical Company of Midland, Mich.), EDTA and NTA (both from BASF Corporation of Florham Park, N.J.), which have a high initial pH, were made by adding the appropriate amount of ferric chloride to the chelants to achieve saturation of available sites on the molecules. Since each of these three chelants had a starting pH of 11, 35% ferric chloride was added until a pH of 4 was attained. The pH was then raised to 7 using sodium hydroxide. Precipitation of iron oxides and/or hydroxides at this pH offered assurance of complete chelation of still soluble iron after 24 hours. A solution of gluconic acid was made by adding sodium hydroxide to 0.3 M solutions until a pH of 11 was attained. The pH was then lowered to 4 using 35% ferric chloride and returned to pH 7 with sodium hydroxide to assure saturation of all chelation sites with ferric ions (Fe oxide precipitate noted after 24 hours).

Total sulfides were tested for using Standard Methods 4500-$S^{2-}$ D with a Hach Chemical Company DR 2000 Spectrophotometer and reagents from Hach specific for this particular test. In order to keep total sulfides within the range of the test, samples were diluted with distilled water prior to conducting the test as per Hach instructions.

A batch of raw influent wastewater from a local wastewater plant was spiked with sulfide to attain a final total sulfide concentration of 13.7 ppm within seven liters of sample in a glass container. The raw wastewater received a dose of 4 ppm of each of the four ferric chelants (mass calculated as chelant) just prior to addition of ozone.

Ozone addition was accomplished using an ozone generator from Ozone Solutions, Sioux Center, Iowa. The generator was capable of generating up to 2 grams per hour of ozone. Injection of ozone into the wastewater was accomplished using an injection system from Ozone Solutions called the H2O-Mini. The unit is designed to treat from 1.5 to 5.7 liters per minute of wastewater. The unit was set up to deliver 6.7 mg/minute of dissolved ozone (assumed the 80% efficiency of dissolution noted by the manufacturer) to wastewater passing the injection nozzle within the H2O-mini. Each test was designed for maximum wastewater flow through the H2O-mini (5.7 liters/min). This meant that the entire 7 liter wastewater volume would pass through the unit every 1.23 minutes with each liter receiving ~0.95 mg of ozone during that time. Using this logic it was determined that it would take ~14.4 minutes for the H2O-mini to deliver 13.7 mg/liter of ozone to each vessel or one weight equivalent to the sulfide present in the wastewater.

The literature suggests that it takes ~3 milligram of ozone to oxidize 1 milligram of sulfide (www.o3water.com/Articles/guideto.htm). An objective of the study will be to treat most, but not all, of the sulfide present within the individual test samples in order to determine which treatment was more efficient than the others. Therefore, each test was designed to run for 14.4 minutes through the ozone injection equipment to obtain approximately one third of the ozone necessary to oxidize all sulfide present within the samples if the ozone is applied alone.

In the ozone experiment that did not include ferric chelants, the wastewater was simply pumped through the ozone injection system for the prescribed period of time. Samples were taken over twenty minutes of contact time from the recirculation vessel after ozonation. For each of the four ferric chelant studies, chelants were added to the wastewater recirculation vessels just prior to starting the injection of ozone and recirculation of the liquids. The injection of ozone was applied over the prescribed period and sampled as before in the ozone only experiment.

The tests resulted in the following tabulated data:

TABLE 23

Comparative Data for the Study

| Contact Time (Minutes) | Ozone only | Fe-Gluconate | Fe-NTA | Fe-EDTA | Fe-HEIDA |
|---|---|---|---|---|---|
| 0 | 13.70 | 13.70 | 13.70 | 13.70 | 13.70 |
| 5 | 8.05 | 3.40 | 3.40 | 6.20 | 6.80 |
| 10 | 7.50 | 2.80 | 1.90 | 5.10 | 6.00 |
| 20 | 7.40 | 1.40 | 1.30 | 4.90 | 5.40 |

*Ozone at ~13.4 ppm with sulfide at 13.7 ppm for all studies.

TABLE 24

Overall total percentage of sulfide reduction by test

| Treatment | Ozone only | Fe-Gluconate | Fe-NTA | Fe-EDTA | Fe-HEIDA |
|---|---|---|---|---|---|
| Percentage Reduction | 46% | 90% | 91% | 64% | 60% |

From these studies it can be concluded that:
1. All studies using ferric chelants indicated improved performance over ozone treatment alone.
2. Ferric gluconate (90% reduction) and ferric NTA (91% reduction) were significantly better in treating sulfides in the presence of ozone than ferric EDTA (64% reduction) and ferric HEIDA (60% reduction).

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of the appended claims. For example, regardless of the content of any portion (e.g., title, field, background, summary, abstract, drawing figure, etc.) of this application, unless clearly specified to the contrary, such as via an explicit definition, there is no requirement for the inclusion in any claim of the application of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all subranges therein. For example, if a range of 1 to 10 is described, that range includes all values therebetween, such as for example, 1.1, 2.5, 3.335, 5, 6.179, 8.9999, etc., and includes all subranges therebetween, such as for example, 1 to 3.65, 2.8 to 8.14, 1.93 to 9, etc. Any information in any material (e.g., a United States patent, United States patent application, book, article, etc.) that has been incorporated by reference herein, is only incorporated by reference to the extent that no conflict exists between such information and the other statements and drawings set forth herein. In the event of such conflict, then any such conflicting information in such incorporated by reference material is specifically not incorporated by reference herein.

What is claimed is:

1. A method for reducing a concentration of a contaminant associated with a medium, comprising treating the medium with ferric gluconate and an oxidizing agent in amounts effective to oxidize at least a portion of the contaminant, wherein the contaminant is an organic compound having at least one aromatic functional group, wherein the oxidizing agent comprises a hydrogen peroxide, persulphate, permanganate, chlorine dioxide, halogen, or mixtures thereof, and wherein the medium is a fluid.

2. The method of claim 1, wherein the medium is a fluid within a space defined at least in part by a structure selected from: tunnel, mine, well, ditch, canyon, cavern, cave, hole, corner, niche, bunker, building, compartment, room, clean room, enclosure, container, tank, pipe, equipment, ship, airplane, vehicle, automobile, and train.

3. The method of claim 1, wherein the oxidizing agent is hydrogen peroxide.

4. The method of claim 1, wherein said treating occurs in situ.

5. The method of claim 1, wherein said treating occurs ex situ.

6. The method of claim 1, wherein said treating occurs at a pH in the range of approximately 5 to approximately 8.

7. The method of claim 1, wherein said treating occurs at approximately a pH of the medium.

8. The method of claim 1, wherein a substantial portion of the contaminant is oxidized.

9. The method of claim 1, further comprising preparing the ferric gluconate.

10. The method of claim 1, further comprising, to improve oxidation, adjusting an operating parameter of at least one item selected from: the ferric gluconate, the oxidizing agent, the medium, and the contaminant.

11. The method of claim 1, further comprising, to improve oxidation, controlling an operating parameter of at least one item selected from: the ferric gluconate, the peroxide compound, the medium, and the contaminant.

12. The method of claim 1, further comprising determining a reduction in the concentration of the contaminant associated with the medium.

13. The method of claim 1, further comprising dispersing a mixture of the ferric gluconate and the oxidizing agent in a form selected from: liquid, foam, solid, gaseous, and aerosol.

14. The method of claim 1, further comprising decontaminating the medium.

15. The method of claim 1, further comprising sanitizing the medium.

16. The method of claim 1, further comprising killing a biological selected from a: mold, fungi, protozoa, amoeba, bacteria, virus, and prion.

17. The method of claim 1, further comprising decomposing waste material containing at least one aliphatic or aromatic functional group.

18. The method of claim 1, further comprising decontaminating a clean room environment.

19. The method of claim 1, further comprising treating the medium to reduce a concentration of iron associated with the medium.

20. The method of claim 1, further comprising repeating said treating of the medium to improve oxidation.

21. The method of claim 1, further comprising adding an organic compound to the medium to improve said method.

* * * * *

UNITED STATES PATENT AND TRADEMARK OFFICE
CERTIFICATE OF CORRECTION

PATENT NO.       : 7,662,294 B1                                  Page 1 of 1
APPLICATION NO.  : 11/047879
DATED            : February 16, 2010
INVENTOR(S)      : Henry Wilmore Cox, Jr.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 432 days.

Signed and Sealed this

Thirtieth Day of November, 2010

David J. Kappos
*Director of the United States Patent and Trademark Office*